(12) United States Patent
Calabrese

(10) Patent No.: US 8,657,768 B1
(45) Date of Patent: Feb. 25, 2014

(54) CERVICAL COLLAR HAVING FLEXIBLE CHIN SUPPORT

(76) Inventor: Salvatore Calabrese, Philadelphia, PA (US)

( * ) Notice: Subject to any disclaimer, the term of this patent is extended or adjusted under 35 U.S.C. 154(b) by 0 days.

(21) Appl. No.: 13/231,352

(22) Filed: Sep. 13, 2011

Related U.S. Application Data

(63) Continuation of application No. 13/187,659, filed on Jul. 21, 2011, now abandoned.

(60) Provisional application No. 61/366,736, filed on Jul. 22, 2010.

(51) Int. Cl.
A61F 5/00 (2006.01)

(52) U.S. Cl.
USPC ..................................... 602/18; 128/DIG. 23

(58) Field of Classification Search
USPC ............................... 602/17–19; 128/DIG. 23
See application file for complete search history.

(56) References Cited

U.S. PATENT DOCUMENTS

| | | |
|---|---|---|
| 2,801,630 A | 8/1957 | Moore |
| 2,806,471 A | 9/1957 | Breese |
| 2,818,063 A | 12/1957 | Smith et al. |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,050,052 A | 8/1962 | Grassl et al. |
| 3,060,930 A | 10/1962 | Grassl |
| 3,075,521 A | 1/1963 | Grassl |
| 3,135,256 A | 6/1964 | Gruber |
| D203,018 S | 11/1965 | Helferich |
| 3,285,244 A | 11/1966 | Cottrell |
| 3,306,284 A | 2/1967 | McKinley |
| 3,313,297 A | 4/1967 | Applegate et al. |
| 3,374,785 A | 3/1968 | Gaylord, Jr. |
| 3,477,425 A | 11/1969 | Grassl |
| 3,504,667 A | 4/1970 | McFarlane |
| 3,512,523 A | 5/1970 | Barnett |
| 3,530,853 A | 9/1970 | Bond |
| 3,572,328 A | 3/1971 | Bond |
| 3,696,810 A | 10/1972 | Gaylord, Jr. |
| 3,756,226 A | 9/1973 | Calabrese et al. |
| 3,916,884 A | 11/1975 | Attenburrow |
| 3,916,885 A | 11/1975 | Gaylord, Jr. |
| 4,099,523 A | 7/1978 | Lowrey |
| 4,401,111 A | 8/1983 | Blackstone |
| 4,413,619 A | 11/1983 | Garth |
| 4,543,947 A | 10/1985 | Blackstone |
| RE32,219 E | 8/1986 | Garth |
| 4,712,540 A | 12/1987 | Tucker et al. |
| 4,955,368 A | 9/1990 | Heimann |
| 4,958,631 A | 9/1990 | Sarkozi |
| 4,987,891 A | 1/1991 | Gaylord, Jr. et al. |

(Continued)

Primary Examiner — Michael A. Brown
(74) Attorney, Agent, or Firm — Blank Rome LLP

(57) ABSTRACT

An improved cervical collar front portion fabricated from an injection molded thermoplastic resin which when used in connection with a back portion is able to secure a wearer's head and neck. The cervical collar can either be a single piece collar with an integral front portion and back portion or as a two-piece collar with the front and back portions as separate and distinct pieces that are connected together. The front portion incorporates a mandible and chin support which is rigid at the distal ends and flexible at the median to accept and accommodate any wearer's uniquely shaped chin. Furthermore, the chin support central portion is essentially perpendicular to the rest of the front collar portion.

14 Claims, 7 Drawing Sheets

(56) References Cited

U.S. PATENT DOCUMENTS

| | | |
|---|---|---|
| 5,029,577 A | 7/1991 | Sarkozi |
| 5,038,759 A * | 8/1991 | Morgenstern .................. 602/18 |
| 5,060,637 A | 10/1991 | Schmid et al. |
| 5,097,824 A | 3/1992 | Garth |
| 5,180,361 A | 1/1993 | Moore et al. |
| 5,211,623 A | 5/1993 | Sarkozi |
| 5,230,698 A | 7/1993 | Garth |
| 5,366,438 A | 11/1994 | Martin, Sr. |
| 5,520,619 A | 5/1996 | Martin |
| 5,588,957 A | 12/1996 | Martin, Sr. |
| 5,593,382 A | 1/1997 | Rudy, Jr. et al. |
| 5,622,529 A * | 4/1997 | Calabrese ...................... 602/18 |
| 5,688,229 A | 11/1997 | Bauer |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A * | 8/1998 | Tweardy et al. ............. 411/339 |
| 5,797,863 A | 8/1998 | Køhnke |
| 5,865,773 A | 2/1999 | Koledin |
| 5,904,662 A | 5/1999 | Myoga |
| 5,993,403 A | 11/1999 | Martin |
| 6,027,467 A | 2/2000 | Nakamura et al. |
| 6,036,664 A | 3/2000 | Martin, Sr. et al. |
| 6,045,523 A | 4/2000 | Donaldson |
| 6,056,711 A | 5/2000 | Domanski et al. |
| RE36,745 E | 6/2000 | Rudy, Jr. et al. |
| 6,071,255 A | 6/2000 | Calabrese |
| 6,090,058 A | 7/2000 | Traut et al. |
| 6,165,146 A | 12/2000 | Giebeler |
| 6,245,033 B1 | 6/2001 | Martin |
| 6,254,560 B1 | 7/2001 | Tweardy et al. |
| 6,423,020 B1 | 7/2002 | Koledin |
| 6,458,090 B1 | 10/2002 | Walpin |
| 6,494,854 B1 * | 12/2002 | Visness et al. .................. 602/18 |
| D475,139 S | 5/2003 | Myoga |
| 6,663,581 B1 * | 12/2003 | Calabrese ...................... 602/18 |
| 6,726,643 B1 | 4/2004 | Martin |
| 6,770,046 B2 | 8/2004 | Hansen |
| 6,926,686 B2 | 8/2005 | Cheatham |
| 7,141,031 B2 * | 11/2006 | Garth et al. ..................... 602/18 |
| 7,309,321 B2 | 12/2007 | Farley et al. |
| 7,371,222 B2 | 5/2008 | Heinz et al. |
| 7,399,288 B2 | 7/2008 | Chao |
| 7,442,176 B2 | 10/2008 | Cojbasic |
| 7,878,995 B2 | 2/2011 | Harty |

* cited by examiner

CERVICAL COLLAR HAVING FLEXIBLE CHIN SUPPORT

RELATED APPLICATIONS

This application is a continuation of U.S. patent application Ser. No. 13/187,659, filed Jul. 21, 2011, which claims the benefit of U.S. Provisional Application No. 61/366,736, filed Jul. 22, 2010, the entire contents of which are incorporated herein by reference.

FIELD OF THE INVENTION

The present invention relates to orthopedic restraints and, in particular to cervical collars utilized for cervical spine immobilization.

BACKGROUND OF THE INVENTION

Cervical collars have been developed to limit the range of motion of the cervical spine of an individual who has sustained trauma to their head and neck as a result from an accident, injury or illness. Orthopedic or rehabilitation style cervical collars offer the wearer optimal comfort, but provide minimal restriction of the range of the individual's cervical motion. Two-piece cervical collars as shown in U.S. Pat. Nos. 5,230,698, 6,254,560 and 7,141,031 incorporate a front portion and a back portion which are mechanically connected together around the neck of a wearer. Each portion is fabricated with an external plastic shell and a removable padded foam inner liner.

Although this type of cervical collar is comfortable to wear due to the padded foam liner, it provides the wearer with marginal range of motion limitations due to the design and connection of the chin support. For instance, the chin support is rigid and allows both a transverse (turning the head left and right) and lateral (moving the head downward to bring the ear closer to the shoulder) range of motion by the wearer. Also, a mechanical connection is made between the chin support and the separate front portion. However, that mechanical connection allows for unwanted movement and a greater range of wearer motion, which reduces cervical spine stabilization. The mechanical connection is also prone to breaking or becoming uncoupled, causing further or secondary injury to the wearer. Moreover, this style of cervical collar is unacceptable for emergency medical use due to its cumbersome semicircular shape which prohibits easy application at the scene of an accident as well as vehicle storage requirements. These orthopedic or rehabilitation cervical collars are costly, cumbersome and do not provide the cervical spine support needed for emergency medical services.

One-piece cervical collars have also been developed, such as those shown in U.S. Pat. Nos. 5,795,315 and 5,622,529. The cervical collar is fabricated with an external plastic shell and a foam inner liner. These emergency medical cervical collars are relatively easy to store and apply at the scene of an accident to a wearer. Although this type of cervical collar is designed to limit the range of motion of a wearer, it provides very little comfort and in many instances discomfort to the wearer due to the rigidity of the chin support which exerts unnecessary pressure on the bottom of the wearer's chin and mandible, causing further or secondary injury to the wearer.

All of these conventional cervical collars have numerous design shortcomings, especially with respect to the chin support. For instance, the, '698, '560 and '031 patents each has a chin support which incorporates a separate stiff flexible plastic material component that has to be mechanically fastened to the front portion. This results in a decrease of cervical spine stabilization which allows the wearer an increase in range of motion. The '529 and '315 patents each has a chin support with a rigid injection molded thermoplastic resin structure which can cause discomfort to the chin and mandible of the wearer.

Therefore, there is a need for an emergency medical cervical collar that will provide a high level of cervical spine immobilization by decreasing the wearer's range of motion while also providing a greater amount of comfort by allowing the chin support to be sufficiently flexible to conform to the shape of the wearer's chin.

Accordingly, it is an object of the present invention to provide a cervical collar with a front portion that contains a chin support that is flexible along its length to accept and accommodate any wearer's uniquely shaped chin.

It is a further object of the present invention to eliminate the need for a separate chin support and a front portion that requires a mechanical fastener connection which impedes unwanted movement and uncoupling and thereby prevents further or secondary injury to the wearer.

It is another object of the present invention to fabricate the chin support without reinforcement or structure and only affixed to the front portion at the chin support distal ends to easily bend and flex to change with each wearer's unique chin shape.

It is a still further object of the present invention is to fabricate the chin support entirely perpendicular to the front portion.

Yet another object of the current invention is to provide a cervical collar with a front portion to include a side opening relief area within close proximately of each chin support which will facilitate and control the bend our curvature of the front portion without distorting the chin support.

And still yet another object of the current invention is to fabricate a cervical collar with injection molded rivet studs to include a unitary connection and eliminate mechanical fasteners which are prone to breaking and uncoupling.

These as well as additional objects and features of the present invention will become apparent to those skilled in the art from an understanding of the following detailed description, drawings and claims.

SUMMARY OF THE INVENTION

In accordance with the present invention there is provided a cervical collar comprising a front portion including a chin support molded from a substantially incompressible thermoplastic resin and a separate compressible, flexible foam strip affixed on one side of the front portion. The chin support is configured to be perpendicular to the front portion and is attached at each distal end to the front portion. Furthermore, the chin support is a thin band or ribbon of material with no means of mechanical bracing, structure or support so that it is sufficiently flexible and can accommodate the unique chin shape of the wearer. The cervical collar also comprises a rear or back portion molded from a substantially incompressible plastic resin and a separate compressible, flexible foam piece affixed on one side of the back portion. The front portion has two sides each with a fastener strip that extends from each side and is matingly engageable with a fastener strip that extends from each side of the back portion which when securely fastened forms a cylindrical shape sufficient to limit the wearer head and neck range of motion.

The invention also provides a cervical collar having an elongated body molded in one piece of substantially incompressible thermoplastic resin having a front portion and a back portion extending from the front portion and a separate compressible, flexible foam strip affixed on one side of the elongated body. The front portion includes a chin support configured to be perpendicular to the front portion, and is attached at each distal end to the front portion. Furthermore, the chin support is a thin band or ribbon of material with no means of mechanical bracing, structure or support so that it is sufficiently flexible and can accommodate the unique chin shape of the wearer. The elongated body is of a certain length and flexibility to be configured into a cylindrical shape sufficient to limit the wearer head and neck range of motion with a fastener strip that extends from the end of the front portion and is matingly engageable with a fastener strip that extends from the end of the back portion.

The invention also provides a cervical collar having a front portion including a chin support molded from a substantially incompressible thermoplastic resin and a separate compressible, flexible foam strip affixed on one side of the front portion. The chin support is configured to be perpendicular to the front portion, and is attached at each distal end to the front portion. Furthermore, the chin support is a thin band or ribbon of material with no means of mechanical bracing, structure or support, so that it is sufficiently flexible and can accommodate the unique chin shape of the wearer. The front portion includes a side opening relief area within close proximately of each chin support which facilitates and controls the bend or curvature of the front portion without distorting the chin support.

DETAILED DESCRIPTION OF THE PREFERRED EMBODIMENTS

Figure 1:
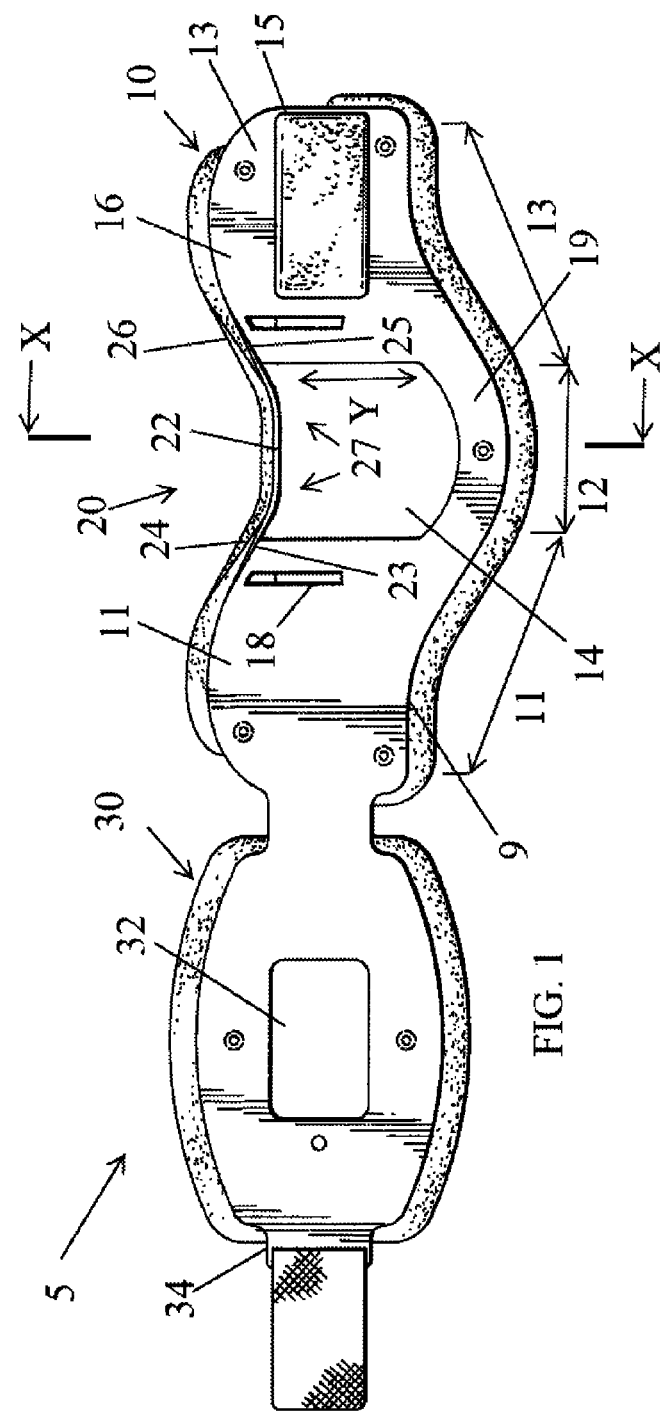
FIG. 1 is a front plan view of a one-piece cervical collar having a flexible chin support in a flat storage state in accordance with the preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

Figure 2:
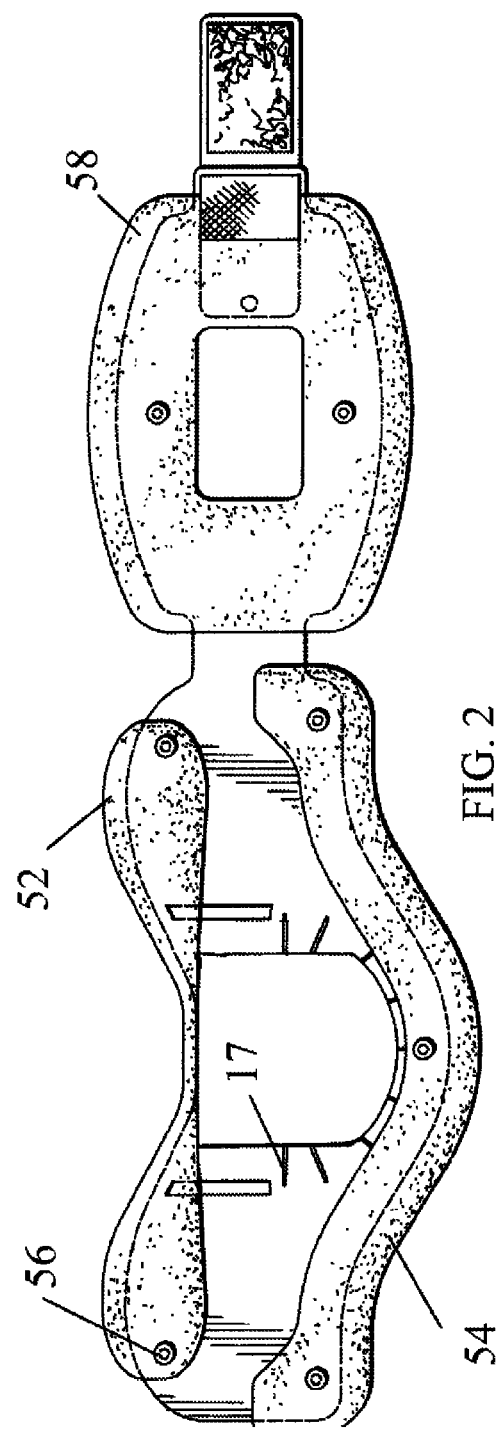
FIG. 2 is a rear plan view of the collar of FIG. 1.

Referring now to the drawings, in which like reference numerals identify like elements throughout the several views, FIG. 1 shows a cervical collar 5 in one embodiment of the present invention. The cervical collar 5 has a front collar body portion 10 and a back collar body portion 30. The front collar portion 10 defines a front face of the collar 5 when in use and the back collar portion 30 forms a back face of the collar 5 when in use. The cervical collar 5 is preferably fabricated by a molding process and is most preferably injection molded in one piece from a lightweight, flexibly resilient, substantially incompressible material such as a suitable thermoplastic resin. The three-dimensional molding process permits the cervical collar 5 to have a contoured profile specifically at the chin area with the remaining front collar areas essentially flat when in the unassembled or storage configuration as shown in FIGS. 1-2.

The front collar body portion 10 generally includes a front central body portion 12 and right and left front side or wing portions 11, 13 on opposite sides of the central body portion 12. The central body 12 includes a chin support 20, a lower central portion 19, and a tracheal opening 14 positioned therebetween. The collar 5 has a top edge which conforms to the shape of the wearer. Thus, the top edge is higher at the wing portions 11, 13 and curves downward toward the central body portion 12 where it leads directly into the tracheal opening 14. The chin support spans the gap otherwise located between the wing portions 11, 13 at an upper portion of the collar 5. The collar 5 also has a bottom edge which is substantially parallel to the top edge to conform to the shape of the wearer.

A first mechanical fastener element 15 is located on one of the wing portions 13 (the right side in the embodiment shown) at a side edge of the front collar portion 10. The first fastener element 15 is coupled with and preferably unitary with the front collar portion 10 and can be fabricated during the injection molding process or by mechanical or chemical means, such as adhesives, rivets, stitching, and welding. The fastener 15 is most preferably a unitary hook shaped molded plastic element fabricated during the injection molding process of the front collar portion 10.

As shown, the front collar portion 10 is preferably generally symmetrical with respect to its midline (i.e., a central transverse line). The entire collar 5 (except for the chin support 20) is essentially flat and coplanar, including the right side wing portion 13, the left side wing portion 11, and the lower central portion 19. The chin support 20 is essentially flat, and extends substantially perpendicular to the rest of the front collar body portion 10. The four portions form and encapsulate the tracheal opening 14, with the side wings 11, 13 forming the sides of the tracheal opening 14, the lower central portion 19 forming the bottom of the tracheal opening 14, and the chin support 20 forming the top of the tracheal opening 14.

As best shown in FIG. 1, the chin support 20 includes a chin support central portion 22 and chin support right/left side portions 24, 26. The chin support central portion 22 is configured to be substantially flat so that it is substantially perpendicular to the plane of the front collar portion 10. The chin support side portions 24, 26, are also flat, but curve upward slightly to be integral with the wing portions 11, 13. The chin support side portions 24, 26 also align with the upper edge of the wing portions 11, 13, respectively. The chin support 20 (and preferably the entire chin support 20 including the central portion 22 and the side portions 24, 26) is formed as a single integral, walled, flexible plastic strip, strap, band or ribbon. The chin support 20 is thin, whereby the thickness of the chin support 20 is much smaller than the width and length of the top surface of the chin support 20 which receives the wearer's chin. The chin support 20 can also have a narrow width and/or length. The chin support 20 is formed integrally with the rest of the front collar body portion 10 by forming the chin support 20 with the front collar body portion 10 during an injection molding process.

Figure 3:
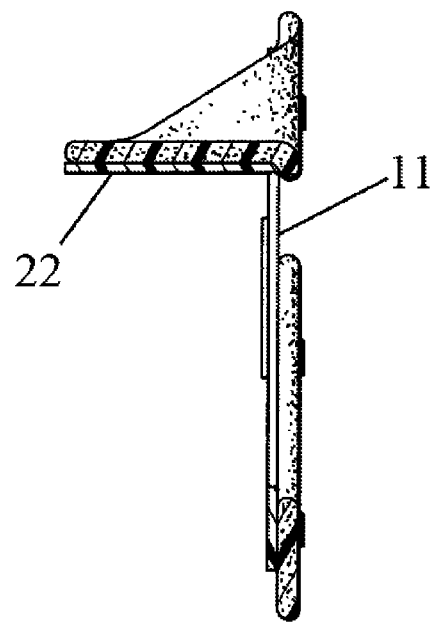
FIG. 3 is a cross-sectional view taken along line X-X of FIG. 1.

Referring to FIG. 3, a cross-section of the chin support 20 taken along the line X-X of FIG. 1 is shown. As illustrated, the chin support central portion 22 extends outward from the front collar wing portions 11, 13 at a right angle (90 degrees) away from the wearer. The chin support side portions 24, 26 also extend outward at a right angle from the immediate areas of the front collar wing portions 11, 13 when flat (FIGS. 1-2) and when assembled for use (FIGS. 5(*a*), 5(*b*)). Accordingly, the chin support 20 forms an L-shape with the front collar wing portions 11, 13. In this manner, the wearer's chin doesn't slide off of the chin support 20, and the chin support 20 forms a more conformed fit to the wearer's chin. When the front collar portion 10 is positioned in an essentially vertical orientation, the chin support 20 is in an essentially horizontal orientation with no transition area or material rotation. It will be apparent that the chin support 20 can also extend slightly inward with respect to the front collar wing portions 11, 13, to form a lopsided T-shaped cross-section (such that the chin support 20 is set back from the inner edge of the front collar wing portions 11, 13 so that the chin support 20 extends to the right and left of the wing portion 11 in the embodiment of FIG. 3).

Figure 4A:
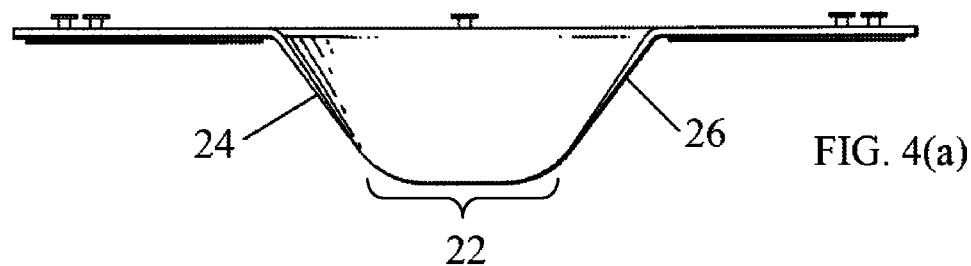
FIG. 4(a) is a top view of the front collar body portion of FIG. 1 without foam.
Figure 4B:
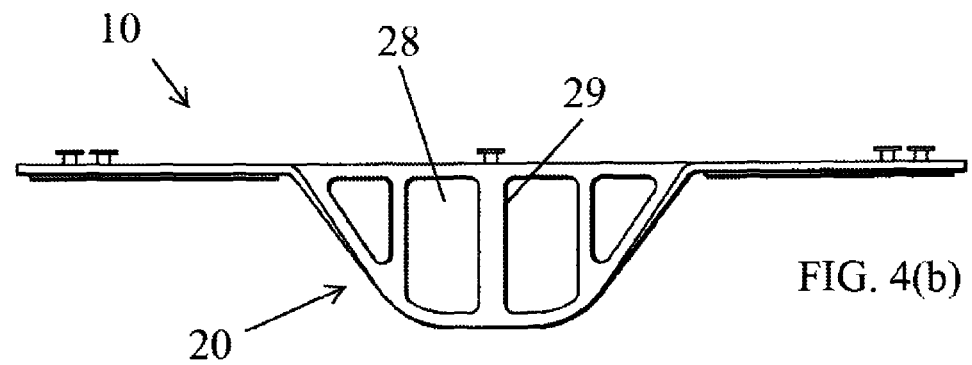
FIG. 4(b) is a top view of the front collar body portion of FIG. 1 having a chin support in accordance with another embodiment of the invention.

As further shown in FIG. 4(*a*), the chin support central portion 22 extends the furthest outward. The chin support side portions 24, 26 lead back to the front collar wing portions 11, 13. The chin support central portion 22 is curved where it leads to the chin support side portions 24, 26 to better conform to the general shape of a wearer's chin. The chin support 20 is preferably thinner than the front body collar portion 10 so that the chin support 20 is more flexible to conform to the shape of the wearer's chin.

Referring to FIG. 4(*b*), the chin support 20 can also have one or more openings 28. Here, four openings 28 are shown which form transverse cross-support members 29. The openings 28 provide for greater flexibility so that the chin support 20 can better conform to the wearer's chin (vertically upward in the embodiment shown). They also provide enhanced comfort for the wearer and make the collar 5 lighter weight. The openings 28 also relieve stress as the collar 5 is bent to the assembled position, and make the collar 5 more adaptive. The openings 28 are preferably arranged so that the cross-support members 29 extend transversely, from the front edge (furthest from the wearer) of the chin support 20 to the rear edge (closest to the wearer) of the chin support 20. This allows the chin support 20 to conform with the manner in which the front body collar portion 10 moves when it is bent to the assembled position. Meanwhile, the cross-support members 29 retain the strength of the chin support 20.

It should be appreciated, however, that the openings 28 can be configured so that the cross-support members 29 extend longitudinally along the chin support 20. In addition, there can be more or less openings 28 provided, or a single large opening 28 can be provided without any cross-support members 29. Still further, the openings 28 need not be provided, but instead the thickness of the chin support 20 can be reduced where the openings are provided. The reduced thickness areas provide greater flexibility with respect to the thicker areas of the chin support 20.

Turning back to FIG. 1, the chin support 20 extends on the front body portion 10 approximately the same length as the tracheal opening 14. The top of the tracheal opening is defined by the chin support central portion 22. That is, there is nothing between the tracheal opening 14 and the perpendicularly-extending chin support central portion 22. It is further noted that at least a portion of the side portions 24, 26 are over the tracheal opening 14 defines the top of the tracheal opening 14. Thus, the chin support 20 does not have any features which provide support in the transverse direction (shown by arrow Y in FIG. 1) to the chin support 20 against the force of the wearer's chin (i.e., vertically upward in the embodiment of FIG. 1). For instance, the chin support 20 (including the central portion 22 and at least a portion of the side portions 24, 26) does not include any stiffeners, transverse bracing or structures either internal or external.

At least a portion of the distal ends of the chin support side portions 24, 26 form attachment sections 23, 25 that are integral with a portion of the upper side wing portions 11, 13 so that the chin support 20 is integral with the front collar body portion 10. Thus, the chin support 20 has attachment sections 23, 25 and a free section 27. The attachment sections 23, 25 comprise a portion of the chin support side portions 24, 26, and preferably less than about one-half of the length of the chin support side portions 24, 26, as shown in FIG. 1. The free section 27 does not have any support in the transverse direction Y other than by virtue of the attachment sections 23, 25.

Thus, the attachment sections 23, 25 have to provide a sufficiently sturdy connection between the chin support 20 and the front collar body portion 10. Accordingly, the attachment sections 23, 25 are integrally molded with the front body collar portion 10 to provide a sturdy and reliable support. The attachment sections 23, are also of sufficient length so that the attachment is sturdy and reliable and does not permit unwanted movement between the chin support 20 and the front collar body section 10. As shown, the attachment sections 23, 25 are linear and elongated and extend along the upper portion of the wings 11, 13. The attachment sections 23, 25 are of sufficient length so that they substantially do not pivot or rotate when the wearer's chin is received, which would otherwise allow the wearer's chin to move in a transverse direction Y or laterally.

The attachment sections 23, 25 are not shown with any transverse support in the embodiments illustrated; however, transverse support can be provided to strengthen that connection such as reinforcements or radiused curves. In addition, the inner sides of the tracheal opening 14 are straight, though the upper portion of the wings 11, 13 can extend slightly into the tracheal opening 14. The chin support 20 portion is substantially perpendicular to the front body side portions 24, 26 at the attachment sections 23, 25 to provide a comfortable fit and avoid the wearer's chin sliding out of the chin support 20.

Figure 5A:
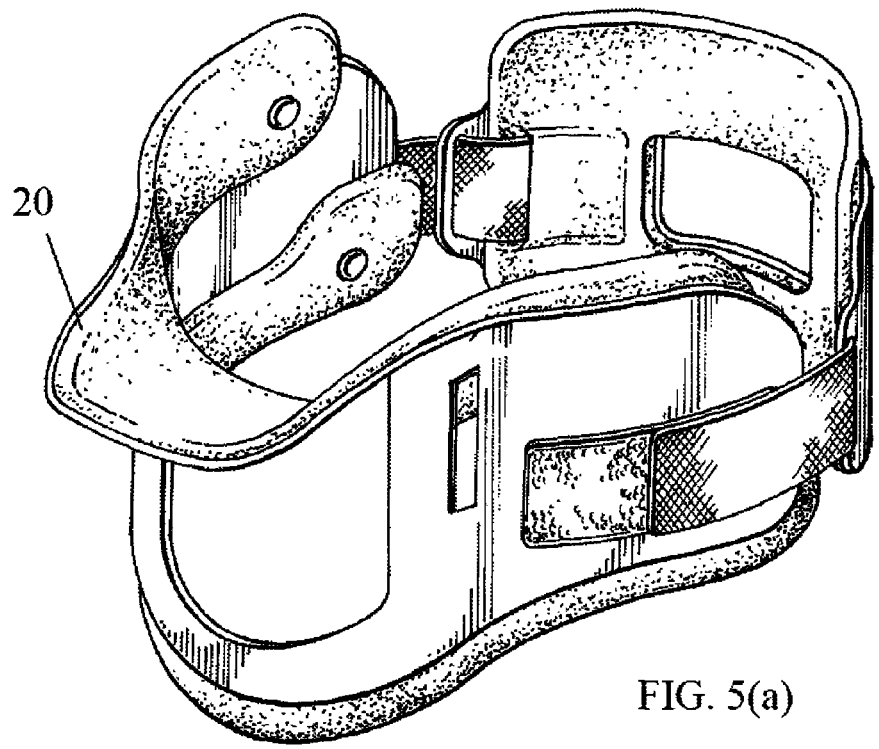
FIG. 5(a) is a perspective view of a two-piece cervical collar assembled in an operational state in accordance with an alternative embodiment of the invention.
Figure 5B:
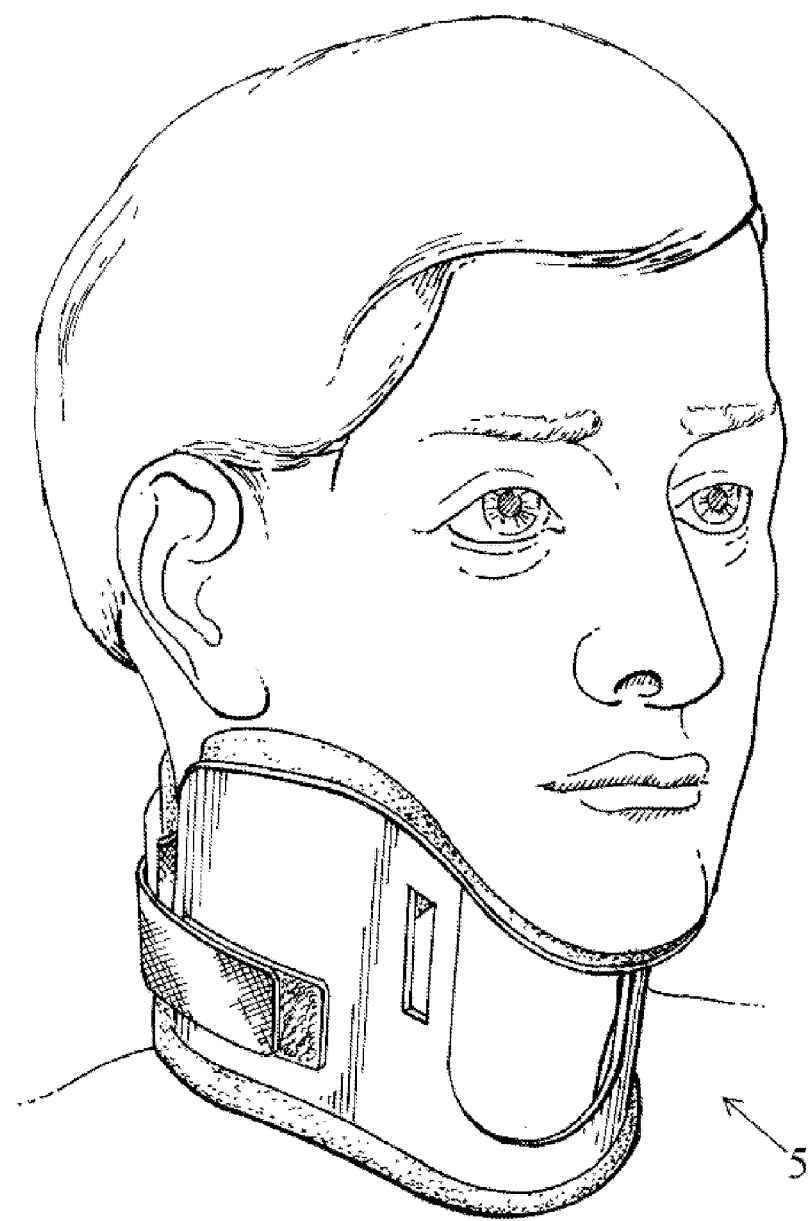
FIG. 5(b) is a perspective view of a two-piece cervical collar assembled on a wearer.
Figure 6:
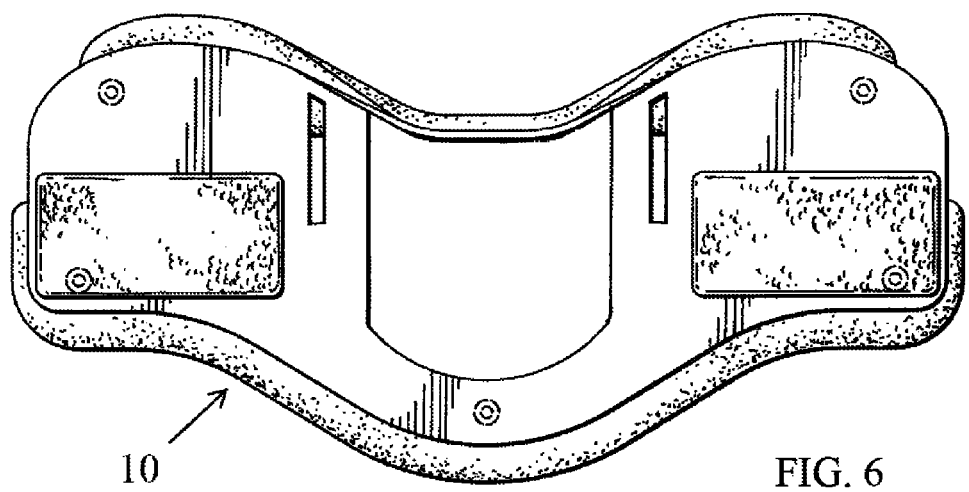
FIG. 6 is a front plan view of the front collar body portion of FIG. 5.
Figure 7:
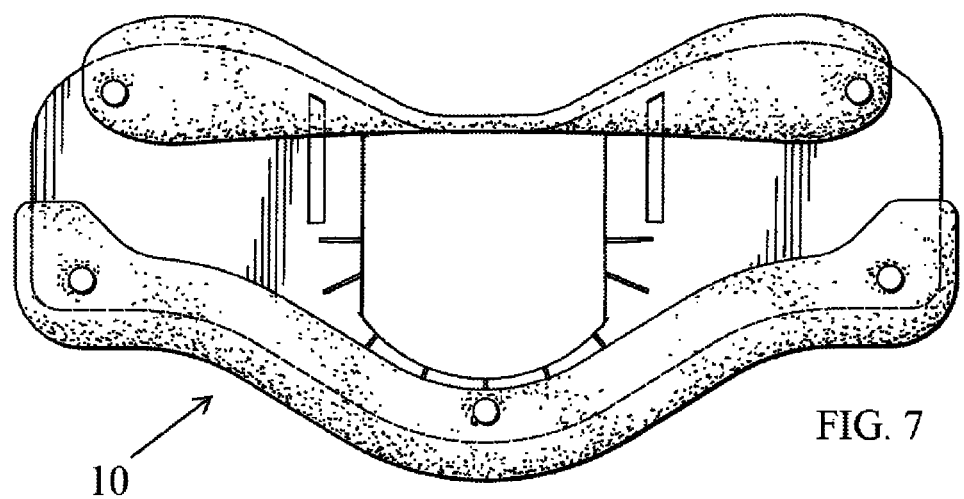
FIG. 7 is a rear plan view of the front collar body portion of FIG. 5.
Figure 8:
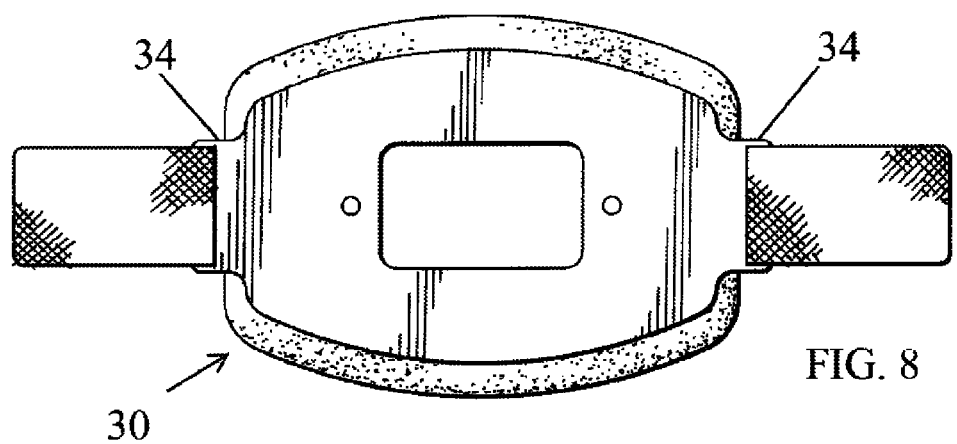
FIG. 8 is a front plan view of the rear collar body portion of FIG. 5.
Figure 9:
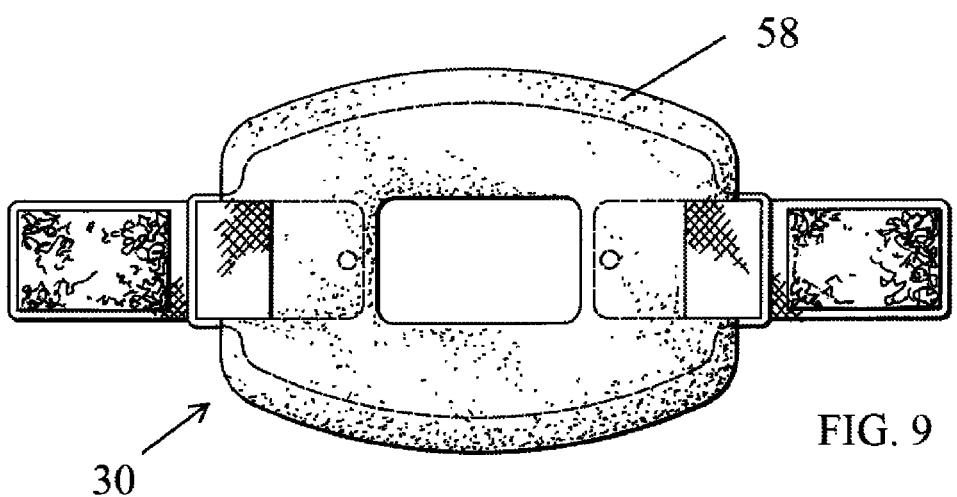
FIG. 9 is a rear plan view of the rear collar body portion of FIG. 5.

As shown in FIG. 1, the attachment sections 23, 25 do not extend into the area above the tracheal opening 14. Accordingly, the free section 27 of the chin support 20 is entirely without transverse support. This allows a sufficient amount of the chin support 20 to be free of the front body portion 10 so that the chin support 20 is highly flexible. Accordingly, when the chin of the wearer is placed in the chin support 20, the free section 27 is extremely flexible to conform to the shape of the wearer's chin as shown in FIG. 5(*b*).

This permits the chin support 20 to freely become configured to accommodate and cradle any wearer's uniquely shaped chin, so that the wearer's chin is in full contact with the chin support 20. The flexibility and configurability of the free section 29 of the chin support 20 is not reduced by any transverse support element. Accordingly, while the chin support central portion 22 is flat when not fitted to the wearer (FIG. 5(*a*)), it becomes curved to conform to the wearer's chin when in use (FIG. 5(*b*)). As illustrated in FIG. 5(*b*), the free section 27 is sufficiently long to wrap up along the sides of the chin. This form fit substantially restricts the transverse and lateral motion of the wearer because the wearer's chin cannot slide along the top surface of the chin support. It also restricts flexion of the head (moving the head forward so that the chin touches the chest). The free section 29 of the chin support 20 is sufficiently long to conform to the shape of the wearer's chin and substantially fix the chin in a central position. The free section 29 should not be overly long to permit the wearer's chin to swing laterally when rested in the chin support 20.

In addition, the chin support 20 is integrally molded with the front collar side portions 11, 13, so that the attachment sections 23, 25 are especially fixed, reliable and strong and do not pivot, rotate or otherwise permit movement. This further allows the chin support 20 to substantially restrict transverse and lateral movement of the wearer's head and neck since the chin and mandible do not float in the chin support 20.

As illustrated, the free section 27 extends across the tracheal opening 14, and the attachment sections 23, 25 extend the entire distance of the overlap between the chin support side portions 24, 26 and the front body side portions 11, 13. However, that entire overlapping portion need not be adjoined to the front body side portion 11, 13. Rather, some of that overlapping portion can be free of the front body side portion 11, 13, so that the free section 27 extends over the front body side portions 11, 13 and is lengthened.

Each of the collar side wing portions 11, 13 includes an upper edge portion 16 which is a stiff and an essentially inflexible area. The upper edge portion 16 provides mandible support since it is in close proximity with the wearer's mandible and restricts lateral and rotational cervical spine movement. Each side portion has a lower edge 9 with is generally contoured to conform to the wearer's clavicle. The lower central potion generally rests on the wearer's sternum.

The back collar body portion 30 is formed unitary with the front collar body portion 10. The back cervical collar body portion 30 defines a back facing side of the collar 5 when in use. It is preferably injection molded in one piece from an incompressible thermoplastic resin, together with the front collar body portion 10. The three-dimensional molding process permits the cervical collar 5 to have a contoured profile, especially at the chin support 20 with the remaining front collar areas essentially flat. The back collar body portion 30 has an opening 32 and a second fastener element 34. The second fastener 34 is positioned at the free edge of the back collar portion 30 and can be any suitable fastener such as strap having VELCRO® type loop material. The second fastener 34 removably engages with the first fastener element 15.

The front collar portion 10 and the back collar portion 30 are sufficiently rigid to support the neck and head of the wearer. In addition, the front collar portion 10 and the back collar portion 30 are each of a sufficient length and flexibility to bend into a semi-circular or U-shape when assembled for use. A two-piece collar in an assembled state of use is shown in FIG. 5 and will be discussed in further detail below. To configure the collar 5 into the assembled state, the free ends of the front and back collar body portions 10, 30 are brought together and the first and second fasteners 15, 34 are mateably engaged. The assembled collar 5 forms a cylindrical or O-shape which can encircle a wearer's neck but is sufficiently rigid to limit the wear's cervical spine range of motion.

The flat storage configuration (FIGS. 1-2) allows the collar 5 to be stored and transported in a flat state. The collar 5 is very compact and multiple collars 5 can be easily stacked and stored on a shelf or in a compartment. The collar 5 can also be quickly and easily placed on a wearer and the fastener elements engaged with one another to form the assembled configuration (FIG. 5).

Referring to FIG. 2, the reverse side of the front collar body portion 10 is illustrated. A compressible foam upper strip 52 and a separate compressible foam lower strip 54 are provided so that the collar 5 is comfortable when worn. The foam strips 52, 54 are mounted to the inside surface of the front collar body portion 10 by suitable means such as a unitarily molded-in rivet stud 56 fabricated during the injection molding process or by mechanical or chemical means, such as adhesives, rivets, stitching, or welding. The rivet stud 56 is fabricated with a unitary shaft and a base through a molding technique which permits raised metal on the first half of the tool to enter openings on the second half of the tool to form the plastic base on front collar body portion 10 without the use of mechanical or secondary assistance. The lower foam 54 is also attached to the front collar body portion 10 by rivet studs or the like. A foam pad 58 is also provided on the inside surface of the back collar body portion 30 and attached by rivet studs or the like.

The tracheal opening 14 is preferably centrally located in the front collar body portion 10. The tracheal opening 14 allows the physician or technician access to the wearer's throat. To maximize the size of the tracheal opening 14, a number of stiffeners 17 are positioned along the inner surface of the front collar body portion 10. The stiffeners 17 are placed about the lower portion of the tracheal opening 14 on the lower central portion 19 and the side wings 11, 13. However, no stiffeners are located on the chin support 20. The stiffeners 17 reinforce the collar to prevent it from collapsing when configured into the semi-circular or U shape and a downward pressure is applied. The stiffeners 17 are short linear pieces which are unitarily molded with and perpendicular to the front collar body portion 10, as shown in FIG. 2.

Referring to FIG. 1 a pair of elongated side relief slots or openings 18 are unitarily molded into the front collar portion 10. The openings 18 are preferably arranged on the front body collar portion 10 to conform with the manner in which the front body collar portion 10 moves to relieve stress when it is bent to the assembled position. Thus, the side relief openings 18 are preferably transversely located and can also be parallel to the sides of the tracheal opening 14. The side relief openings 18 are approximately the same length as the side portion inner edge of the tracheal opening 14. The side relief openings 18 extend from just inside the top edge of the front collar wing portions 11, 13 to about midway of the tracheal opening 14, as illustrated. However, the side relief openings 18 can extend the entire height of the front collar side portions 11, 13, from the top edge to the bottom edge. The side relief openings 18 are positioned just inside the distal ends of the chin support sides 24, 26. The side relief openings 18 relieve any stress placed on the front collar portion 10 when the collar 5 is configured into the semi-circle or U-shape assembled state. That makes it easier to bend the front collar portion 10 without the plastic material stressing and cracking or requiring undue force.

FIGS. 1-2 show the collar 5 in a one-piece configuration where the front collar body portion 10 is unitary with the back collar body portion 30. FIGS. 5-9 show the collar 5 as a two-piece collar whereby the front collar body portion 10 is separate and distinct from the back collar body portion 30. The front collar body portion 10 can then be injection molded separately from the back collar body portion 30. In addition, a first fastening element 15 is placed at both sides of the front collar body portion 10, and a second fastening element 34 is placed at both sides of the back collar body portion 30. Thus, during assembly of the collar 5, both sets of fastening elements 15, 34 are removably attached to each other.

Accordingly, a cervical collar 5 is provided with front and back collar body portions 10, 30 fabricated from injection molded thermoplastic resin which is rigid to provide support to the wearer's head and neck. The chin support 20 is a very flexible strap which extends perpendicular to the front collar body portion 10. The chin support 20 has a center 22 which has no support in the transverse direction Y, and distal attachment sections 23, 25. The chin support 20 is therefore highly configurable to the wearer's chin to provide greater comfort. The chin support 20 is preferably made of a thermoplastic resin which is injection molded together with the front collar body portion 10 so that the attachment sections 23, 25 are integral with the front collar body portion 10.

The foregoing description and drawings should be considered as illustrative only of the principles of the invention. The invention may be configured in a variety of shapes and sizes and is not intended to be limited by the preferred embodiments. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A cervical collar to support a chin, neck and head of a wearer, said collar comprising:
   a front collar portion made from injection molded incompressible material in an essentially flat configuration, said front collar portion having a sufficient length to bend into a semi-circular shape;
   a flexible chin support having distal ends integrally coupled with said front collar portion and a central chin support between the distal ends, said chin support comprising a thin strip made from a flexible material so that said chin support readily conforms to the chin of the wearer, wherein support for said chin support is only provided by the distal ends, wherein said chin support has a thickness which is smaller than a thickness of said front collar portion;
   a back collar portion made from injection molded incompressible material in an essentially flat configuration, said back collar portion having a sufficient length to bend into a semi-circular shape; and,
   a fastener for removably coupling said front collar portion to the back collar portion to encircle the neck of the wearer.

2. The collar of claim 1, wherein said chin support is non-structural.

3. The collar of claim 1, wherein there are no structural elements which support said chin support.

4. The collar of claim 1, wherein said front collar portion and said central chin support is free of said front collar portion.

5. The collar of claim 1, wherein said chin support is substantially perpendicular to the front collar portion.

6. The collar of claim 1, further comprising a side relief opening located on each side of the front collar portion, said side relief opening reducing stress when said front collar portion is bent into the semi-circular shape.

7. The collar of claim 1, further comprising a compressible flexible foam pad on at least one side of each of said front collar portion and said back collar portion.

8. The collar of claim 1, said fastener comprising a first fastener strip affixed to the front collar portion and a second fastener strip affixed to the back collar portion which removably engages said first fastener strip.

9. The collar of claim 1, further comprising a tracheal opening positioned immediately below at least a portion of said chin support.

10. The collar of claim 9, further comprising unitarily molded reinforcement ribs configured perpendicular to an inside surface of said front collar portion about the tracheal opening to stiffen the front collar portion about the tracheal opening and prohibit flexing about the tracheal opening.

11. The collar of claim 1, further comprising unitarily molded rivet studs which are perpendicular to an inside surface of said front collar portion to affix fasteners and foam padding to the inside surface of said front collar portion.

12. The collar of claim 1, further comprising openings in said chin support to increase flexibility of said chin support.

13. The collar of claim 1, wherein said chin support and said front collar portion are injection molded together to be integral with each other.

14. The collar of claim 1, wherein said chin support is made from an incompressible material.

* * * * *